United States Patent [19]

Murphy

[11] Patent Number: 5,074,300
[45] Date of Patent: Dec. 24, 1991

[54] REUSABLE FABRIC-COVERED HEAT-EXCHANGE BAG

[75] Inventor: Edward Murphy, Hatboro, Pa.

[73] Assignee: SePro Healthcare Inc., Montgomeryville, Pa.

[21] Appl. No.: 444,689

[22] Filed: Dec. 1, 1989

[51] Int. Cl.$^5$ .................................................. A61F 7/00
[52] U.S. Cl. .................................. 128/402; 128/403; 383/37; 383/107; 383/901
[58] Field of Search ............... 383/901, 117, 107, 37; 62/530; 128/402, 403, 399, 380; 126/209, 263

[56] References Cited

U.S. PATENT DOCUMENTS

| | | | |
|---|---|---|---|
| 1,603,001 | 10/1926 | Carter | 128/402 |
| 3,244,210 | 4/1966 | Clarizio | |
| 4,243,041 | 1/1981 | Paul | 128/403 |
| 4,385,950 | 5/1983 | Hubbard | |
| 4,700,706 | 10/1987 | Münch | 128/403 |
| 4,832,031 | 5/1989 | Last | 128/402 |
| 4,908,248 | 3/1990 | Nakashima et al. | 62/530 |
| 4,910,978 | 3/1990 | Gordon et al. | 62/530 |

FOREIGN PATENT DOCUMENTS

| | | | |
|---|---|---|---|
| 0162583 | 1/1985 | European Pat. Off. | |
| 1383536 | 3/1972 | United Kingdom | |
| 1495366 | 12/1977 | United Kingdom | 62/530 |

*Primary Examiner*—Edward M. Coven
*Assistant Examiner*—Mark S. Graham
*Attorney, Agent, or Firm*—Synnestvedt & Lechner

[57] ABSTRACT

A reusable, fabric-covered heat exchange bag is provided which includes a thermoplastic waterproof liner means having an interior containment area and an opening for receiving a hot or cold medium, such as hot water or ice. Disposed on a significant portion of the exterior surface of the liner is a thermoplastic fabric-like cover which is joined to the liner to define a peripheral region of the reusable heat exchange bag. The heat seal arrangement which forms the peripheral region of the bag also facilitates the severing of the reusable heat exchange bag from a sheet of stock material.

21 Claims, 3 Drawing Sheets

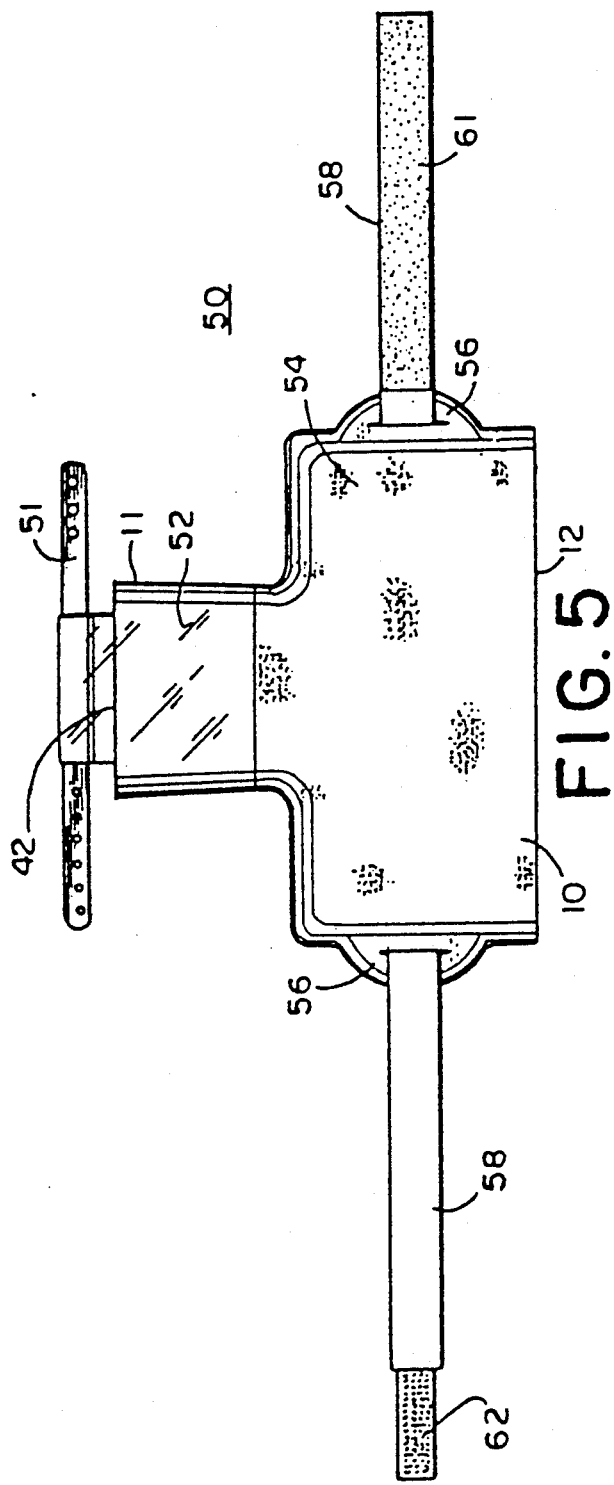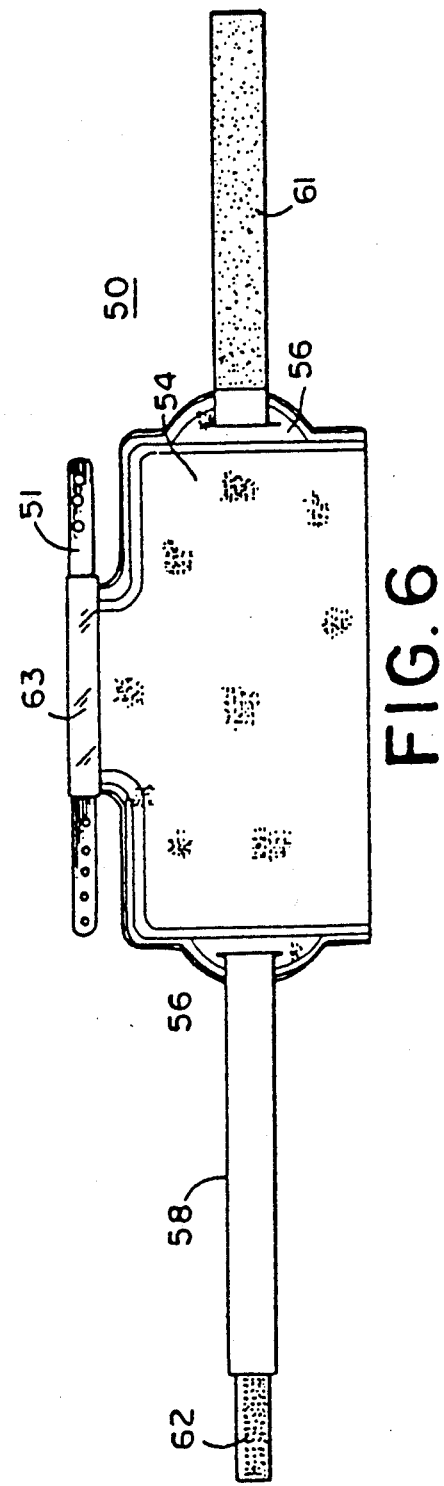

REUSABLE FABRIC-COVERED HEAT-EXCHANGE BAG

CROSS REFERENCE TO RELATED APPLICATION

This application is related to Ser. No. 444,680, filed on Dec. 1, 1989, by Edward A. Murphy, which application is commonly owned with the instant application and which is hereby incorporated by reference.

FIELD OF THE INVENTION

This invention relates to thermoplastic bags for holding hot or cold substances, and more particularly, to providing facilitated means for constructing fabric-covered ice bags and the like.

BACKGROUND OF THE INVENTION

Inexpensive, reusable ice bags have become a popular item for the treatment of patients requiring the application of hot or cold temperatures to localized areas, such as in the treatment of swelling and muscle tears. As such, these products provide a heat exchange from or to the area being treated, see Clarizio, U.S. Pat. No. 3,244,210, Hubbard, et al., U.S. Pat. No. 4,385,950; Turner, British Patent Specification 1 383 536; and European Patent Application Abstract 0162583 all of which are hereby incorporated herein by reference.

Clarizio discloses an early commercial plastic bag, made from a thermoplastic film, such as polyethylene, and includes a neck having an opening for receiving hot or cold substances. The bag may include a single layer of imitation chamois, cellucotton, or other material, folding around the lower portion of the bag beneath the neck and covering both sides of the bag. The heat sealing die alone is suggested as being satisfactory for sealing this cover to the bag film.

Hubbard, et al., discloses a waterproof polyethylene bag having an outer layer of absorbent material perforated by many tiny apertures. The absorbent material can be sonically welded to the polyethylene envelope. This reference primarily deals with saving polyethylene stock by simultaneously cutting tie strings for two adjoining bags.

Turner discloses a hot or cold pack containing reactive chemicals separated by a thin membrane, which when ruptured, permits the chemicals to mix and create the desired temperature effect. This reference discloses that the outer layer of the pack can include moisture-absorbent material.

The European abstract refers to a compress having a polyethylene plastic sack covered with a fabric of knitted polyester. The compress can be provided with a bandage for securing it to a patient.

While in the main, these prior art heat exchange bags provide a viable means for applying ice or hot fluids to localized areas of a patient, there remains a need for a less expensive and more efficiently produced ice bag and a method of manufacturing such bags which reduces the number of costly manual steps.

SUMMARY OF THE INVENTION

This invention provides a reusable heat exchange bag suitable for use in treating patients. The bag includes a thermoplastic waterproof liner having a containment area for a hot or cold medium, such as hot water or ice. The liner is substantially covered with a thermoplastic fabric which is joined to the liner by a heat seal. The heat seal of this invention defines a peripheral region of the heat exchange bag and also provides means for facilitating the severing of the heat exchange bag from a sheet of stock material.

Accordingly, this invention provides a method of manufacturing a novel fabric-covered heat exchange bag in which a single heat sealing operation provides the peripheral regions of the bag as well as a tear initiation line for severing the bag from thermoplastic stock material. This procedure eliminates a separate cutting die operation whereby the bag would normally be severed from stock material.

After heat sealing the heat exchange bag of this invention, the bag can be torn manually or mechanically from the stock material in a simple fluid motion. The resulting heat exchange bag will have a fine taper along the outside edge or heat seal region of the bag. This taper evidences the method by which the bag is manufactured.

In preferred embodiments of this invention, the means for severing the reusable heat exchange bag from the thermoplastic stock material includes a substantially non-fibrous polyethylene heat seal of less than about 1 mil. in thickness. This feature of the extreme edge of the bag permits tearing without attendant fibrous resistance or damage to the heat exchange bag itself.

BRIEF DESCRIPTION OF THE DRAWINGS

The accompanying drawings illustrate preferred embodiments of the invention according to practical application of the principles thereof and in which:

FIG. 5: is a top elevation view of the preferred heat exchange bag of this invention;

FIG. 6: is a top elevation of the preferred heat exchange bag of this invention after the neck has been rolled down to effect a watertight closure;

DETAILED DESCRIPTION OF THE INVENTION

Figure 1:
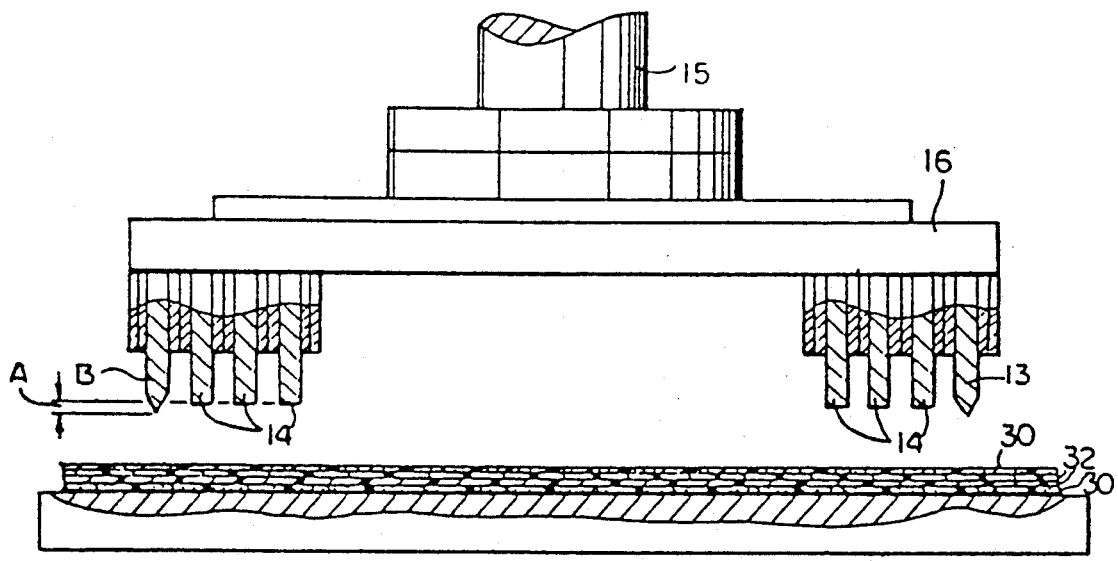
FIGS. 1-3: illustrate in diagrammatic side sectional views, a preferred rule die (1) descending upon thermoplastic stock, (2) heat sealing and producing a tear initiation line, and (3) being removed from the deformed stock material.

The reusable heat exchange bag of this invention is ideally suited for the treatment of patients in hospitals. It also has numerous household or industrial usages, such as refrigerator storage of liquids and food or any other suitable application where a waterproof bag or container is desirable.

The preferred reusable heat exchange bag of this invention includes a thermoplastic waterproof liner means having an interior containment area and an exterior surface thereon. The liner means further has an opening for receiving a hot or cold medium, such as hot water or ice. Disposed on a significant portion of the exterior surface of the waterproof liner is a thermoplastic fabric-like cover means. The fabric-like cover means and the waterproof liner means are joined by heat seal means which defines a peripheral region of the reusable heat exchange bag. This heat seal means also provides means for facilitating the severing of the reusable heat exchange bag from a sheet of stock material.

In a more detailed embodiment of the heat exchange bag, a waterproof polyethylene film liner having an interior containment area and an exterior surface is provided. The liner includes an opening for receiving a hot or cold medium and further includes a non-woven polyethylene fabric cover disposed on a significant portion of its exterior surface. The liner and the cover are joined together along a peripheral region of the reusable heat exchange bag by a plurality of heat seals. At least one of these heat seals includes a tapered edge comprising a substantially non-fibrous polyethylene heat seal of less than about 1 mil.

In the preferred method of this invention a reusable heat exchange bag is manufactured from thermoplastic stock. The method first provides a waterproof film means and a fabric-like material means from the thermoplastic stock. Next, the fabric-like material means is folded along a fold line whereby a substantial portion of the waterproof film means is disposed within the fabric-like material means. The fold line comprises a first edge of the reusable heat exchange bag when the bag is in a flattened condition. Next, the waterproof film means and the fabric-like material means are heat sealed to form a closure with the fold line while simultaneously providing a tear initiation site for facilitating the severing of the reusable heat exchange back from the thermoplastic stock.

With reference to FIG. 5, there is described a reusable heat exchange bag 50 having a substantially rectangular body part 10 with a relatively long neck 11 projecting from one side and defining an opening 42 into the bag. This entrance passage can be provided by having one side of the neck 11 extend outwardly a short distance beyond the other side to facilitate filling of the bag. The bag preferably includes a thermoplastic waterproof liner 52 made of thermoplastic film or sheet material such as polyethylene, rubber hydrochloride, vinyl, or any other suitable thermoplastic, heat sealable film or sheet material. Such material comprises the interior containment area and is made to be substantially waterproof. In the preferred embodiment, the liner comprises a two-ply polyethylene sheet or tube of about 1-5 mils.

Disposed on a significant portion of the exterior surface of the thermoplastic waterproof liner 52 is a thermoplastic fabric-like cover 54. Preferably the fabric-like cover is disposed substantially on the rectangular body part 10 and forms a comfortable surface against the skin of a wearer, when said reusable heat exchange bag is employed for therapeutic purposes. Preferably this fabric-like cover 54 includes a non-woven polyethylene fabric, such as 6725 SCOTT (28 gm/yd$^2$), which is folded around a portion of the preferred two-ply polyethylene sheet. The non-woven fabric can include an embossed surface and preferably is water resistant while also being permeable to sweat or water condensation forming on the skin of the patient. The preferred non-woven fabric of this invention includes a thickness of about 1-5 mils. and is preferably heat sealed or sonically sealed to the preferred thermoplastic waterproof liner 52 to form the peripheral region of bag.

The reusable heat exchange bag 50 of this invention also can include apertured tab means 56 preferably formed by portions of the thermoplastic waterproof liner and fabric-like cover. They are preferably disposed at opposite ends of the rectangular body part 10 of the heat exchange bag 50. A fastening strap 58 having VELCRO® elements 61 and 62 can be disposed through the apertures of the tabs 56 for application of the heat exchange bag 50 to an arm, leg or head of patient.

The heat exchange bag 50 of this invention can be readily filled with a hot or cold medium through opening 42 and then sealed by rolling the closure element 51 along with neck portion 11 and then sealing the closure element to provide a water-tight containment area. VELCRO® or pressure sensitive adhesive attachment mechanisms can also be employed to seal the opening 42 of the heat exchange bag 50.

The heat exchange bag 50 of this invention is preferably made of thermoplastic film or sheet material purchased in tubular form of indefinite length, such as POLY ROLLSTOCK from SealCraft Packaging Corp. If a tube of the material is employed, it is preferably flattened and folded in an intermediate region so that one flap terminates short of the edge on the other flap a distance sufficient to provide the extension on one side of the neck 11. When the tube is so folded, the bottom edge of the bag is formed by a fold line 12, which incidentally preferably corresponds to the fold line of the fabric-like cover 54. The side edges of the bag are preferably formed by heat seals which unite all four polyethylene film plies of material, in addition to two-plies of the fabric-like material. There is no heat seal along the opening 42 of the bag, so that the bag can be filled with contents.

Figure 2:
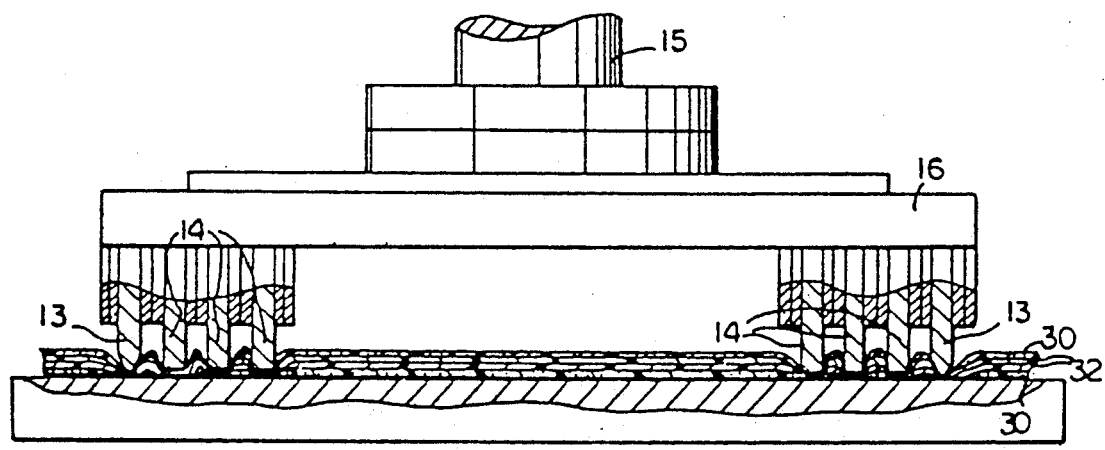
Figure 3:
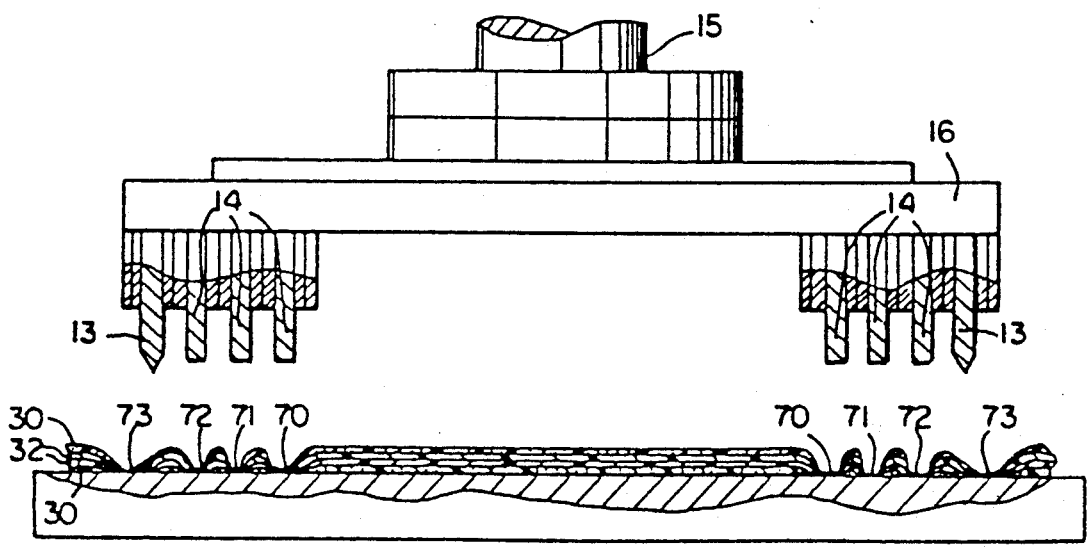
Figure 7:
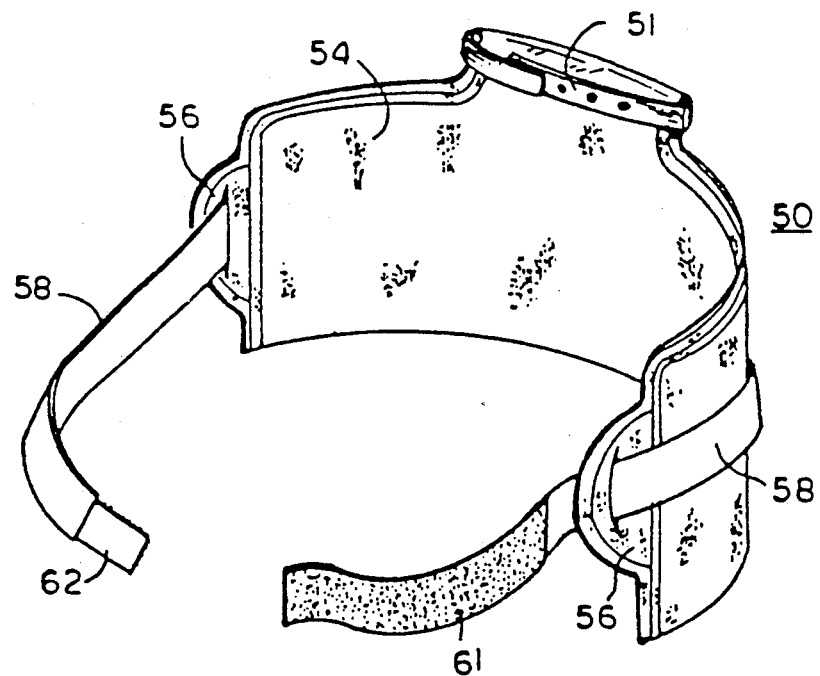
FIG. 7: discloses the preferred embodiment heat exchange bag fully closed and ready for application to a patient via a VELCRO ® fastening strap.

With reference to FIGS. 1-3 there is diagrammatically shown a "rule die" of this invention particularly suited for the purposes of simultaneously creating a heat seal, while providing a tear initiation site for severing the bag from stock material. The rule die preferably comprises brass, copper, or other heat-conductive metals. It also includes a plurality of heat seal elements 14 along with a sharpened heating element 13 which is preferably extended a distance "A" from the ends of heat seal elements 14. Preferably this distance "A" is about 1-3 mils.

In the manufacturing of these bags, an endless stock tube of polyethylene waterproof film 32 is folded and layered with a fabric-like material 30 to form a multi-layer thermoplastic stock. The multi-layer thermoplastic stock can be layered with sheets of mylar on both the top and bottom surfaces, as is common in the art, for avoiding direct contact between the rule die and the molten polyethylene during seal formation. The stock can be disposed over a bottom plate of a preferred high frequency electronic heat sealing press 15. The rule die used in the press is shaped according to the outline of the heat exchange bag and mounted to plate 16. The rule die forms the heat seals which include the outline for the rectangular body part 10, relatively long neck portion 11, and apertured tabs 56. See, Clarizio, cols. 3 and 4 for a disclosure of known manufacturing steps as applied to a polyethylene liner.

Figure 4:
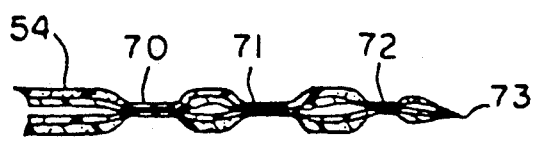
FIG. 4: is a diagrammatic side sectional view of a peripheral edge of the preferred embodiment heat exchange bag after the bag has been torn from stock material.

In accordance with the following description, a novel approach to sealing a fabric-like polyethylene cover to a waterproof polyethylene liner will be described. The sealing of the cover to the liner of this invention is particularly difficult and requires extreme sensitivity to manufacturing tolerances and conditions. If insufficient pressure or temperature is employed, the tear initiation seal 73 described in FIGS. 3, 4 and 8 will not be thin enough or non-fibrous enough to enable the bag to readily tear it from the thermoplastic stock. On the other hand, if the temperature and/or pressure exceeds certain set limits, heat seals 70 and 71 may become defective, the bag containment area may become violated and subsequent tearing of the heat exchange bag from the stock material may cause damage to the bag, stock material or both.

It has been discovered that the combination of non-woven polyethylene cover and a two-ply polyethylene tube liner provide the ideal materials for constructing the heat exchange bag. It is noted that the non-woven nature of the polyethylene cover permits standard manufacturing equipment to adhere it to the polyethylene film liner, if proper considerations are given for time, temperature and pressure conditions. It has been discovered that a rather narrow range of operating pressures and temperatures enable both a sound heat seal for producing a containment area while simultaneously producing a tear initiation site along the periphery of the bag. The preferred conditions include a temperature of about 350°–425° F.; preferably 425°–475° F. and most preferably about 450° F. The ideal times for applying the heating elements 13 and 14 include a range of 1.5–3.5 sec., preferably 2–3 sec. and most preferably about 2.5 sec. Acceptable pressures for the preferred method include about 85–110 psi, preferably about 95–105 psi, and most preferably about 100 psi. Operating within these suitable ranges eliminates a separate cutting step, and a more cost effective bag can be produced.

Figure 8:
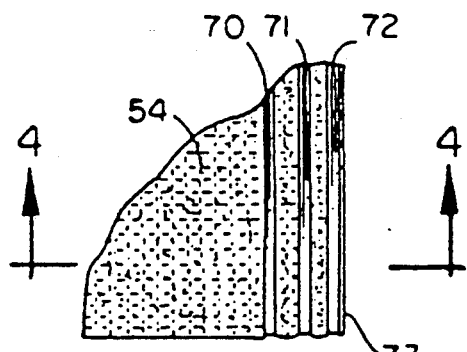
FIG. 8: is an enlarged detail of the heat seal region of the preferred embodiment heat exchange bag of FIG. 5.

It is further noted upon close examination of the preferred heat seals 70, 71, 72 and 73 of this invention in FIG. 8, that the heat sealing within the preferred range of operating conditions substantially degrades the fibrous nature of the non-woven polyethylene cover 54, to produce generally translucent heat seals. Since the sharpened heating element 13 of the rule die 16 preferably extends downwardly a definite distance from the heat seal elements 14, the particular thickness of material at heat seal 73 is less than seals 70, 71 and 72 and preferably less than about 1 mil. Thus, upon mechanical or manual tearing of the heat exchange bag from the stock material, a clean demarcation line is formed about the peripheral edge of the bag and a slight taper is evidenced, as described in FIG. 4. This is believed to be made possible because the tough, non-woven polyethylene fabric-like material becomes partially decomposed and forms a rather translucent heat seal 73, which is easily severed.

From the foregoing, it can be realized that this invention provides improved heat exchange bags and methods for manufacturing these bags more efficiently. Although various embodiments have been illustrated, this was for the purpose of describing, but not limiting, the invention. Various modifications, which will become apparent to one skilled in the art, are within the scope of this invention described in the attached claims.

What we claim:

1. A reusable heat exchange bag, comprising:
   thermoplastic waterproof liner means having an interior containment area and an exterior surface thereon, said liner means having an opening for receiving a hot or cold medium, including hot water or ice;
   thermoplastic fabric cover means disposed on a significant portion of said exterior surface; said thermoplastic fabric cover means and said thermoplastic waterproof liner means joined by heat seal means, said heat seal means defining a peripheral region of said reusable heat exchange bag and comprising tear means comprising a substantially non-fibrous thermoplastic heat seal for substantially simultaneously facilitating the severing of said reusable heat exchange bag from a sheet of thermoplastic waterproof stock material and a sheet of thermoplastic fabric stock material.

2. The reusable heat transfer bag of claim 2 wherein said liner means comprises polyethylene.

3. The reusable heat transfer bag of claim 1 wherein said polyethylene comprises a thickness of about 1–5 mils.

4. The reusable heat exchange bag of claim 2 wherein said liner means comprises a two-ply polyethylene sheet.

5. The reusable heat exchange bag of claim 3 wherein said thermoplastic fabric cover means comprises polyethylene.

6. The reusable heat exchange bag of claim 4 wherein said thermoplastic fabric cover means comprises a non-woven polyethylene fabric folded around a portion of said two-ply polyethylene sheet.

7. The reusable heat exchange bag of claim 6 wherein said non-woven fabric comprises an embossed surface.

8. The reusable heat exchange bag of claim 7 wherein said non-woven fabric is water resistant.

9. The reusable heat exchange bag of claim 8 wherein said non-woven fabric is permeable to water condensation.

10. The reusable heat exchange bag of claim 9 wherein said non-woven fabric comprises a thickness of about 1–5 mils.

11. The reusable heat exchange bag of claim 2 wherein said heat seal means comprises a plurality of heat seals disposed along said peripheral region.

12. The reusable heat exchange bag of claim 11 wherein said plurality of heat seals adhere said thermoplastic fabric cover means to said thermoplastic waterproof liner means along at least a pair of opposite sides of said heat exchange bag.

13. The reusable heat exchange bag of claim 12 wherein said thermoplastic waterproof liner means and said thermoplastic fabric-like cover means are heat sealed to form apertured tab means disposed at said opposite sides of said reusable heat exchange bag.

14. The reusable heat exchange bag of claim 13 wherein said apertured tab means comprises a fastening strap disposed through said apertures.

15. The reusable heat exchange bag of claim 1 wherein said tear means comprises a tapered edge of said heat seal means.

16. The reusable heat exchange bag of claim 15 wherein said tapered edge comprises a substantially non-fibrous polyethylene heat seal.

17. The reusable heat exchange bag of claim 15 wherein said tapered edge comprises a thickness of less than about 1 mil.

18. A reusable heat exchange bag, comprising:
   (a) a waterproof polyethylene film liner having an interior containment area and an exterior surface thereon, said liner having an opening for receiving a hot or cold medium, including hot water or ice; a non-woven polyethylene fabric cover disposed on a significant portion of said exterior surface, said liner and said cover joined together along a peripheral region of said reusable heat exchange bag by a plurality of heat seals, at least one of said plurality of heat seals disposed for substantially simultaneously facilitating the severing of said bag from a waterproof polyethylene film source and a nonwoven polyethylene fabric source, and upon said severing, comprising a tapered edge comprising a substantially non-fibrous polyethylene heat seal of less than about one mil.

19. An intermediate article of manufacture, comprising:
thermoplastic waterproof liner means having an interior containment area and an exterior surface thereon;
thermoplastic fabric cover means disposed on a significant portion of said exterior surface, said thermoplastic fabric cover means and said thermoplastic waterproof liner means joined by heat seal means defining an outline of said reusable heat exchange bag on said intermediate article, said heat seal means comprising a substantially continuous non-fibrous heat seal for facilitating the severing by substantially simultaneously tearing of said reusable heat exchange bag from a remaining portion of said thermoplastic fabric cover means and said thermoplastic waterproof liner means.

20. The intermediate article of claim 19 wherein said heat seal means comprises a polyethylene heat seal of less than about 1 mil.

21. The intermediate article of claim 20 wherein said thermoplastic fabric-like cover means is adhered to said thermoplastic waterproof liner means by a plurality of heat seals.

* * * * *